(12) United States Patent
Keahey et al.

(10) Patent No.: US 11,803,951 B2
(45) Date of Patent: Oct. 31, 2023

(54) HIGH RESOLUTION MICROENDOSCOPE EMPLOYING DIFFERENTIAL STRUCTURED ILLUMINATION AND METHOD OF USING SAME

(71) Applicant: William Marsh Rice University, Houston, TX (US)

(72) Inventors: Pelham Keahey, Missouri City, TX (US); Rebecca Richards-Kortum, Houston, TX (US)

(73) Assignee: William Marsh Rice University, Houston, TX (US)

(*) Notice: Subject to any disclaimer, the term of this patent is extended or adjusted under 35 U.S.C. 154(b) by 0 days.

(21) Appl. No.: 18/055,237

(22) Filed: Nov. 14, 2022

(65) Prior Publication Data
US 2023/0222637 A1    Jul. 13, 2023

Related U.S. Application Data

(63) Continuation of application No. 15/957,442, filed on Apr. 19, 2018, now abandoned, which is a continuation of application No. PCT/US2016/057599, filed on Oct. 19, 2016.

(60) Provisional application No. 62/243,323, filed on Oct. 19, 2015.

(51) Int. Cl.
| | | |
|---|---|---|
| A61B 1/06 | (2006.01) |
| G06T 5/50 | (2006.01) |
| A61B 1/07 | (2006.01) |
| G02B 23/24 | (2006.01) |
| A61B 1/04 | (2006.01) |
| G06T 5/00 | (2006.01) |

(52) U.S. Cl.
CPC .............. G06T 5/50 (2013.01); A61B 1/042 (2013.01); A61B 1/043 (2013.01); A61B 1/0646 (2013.01); A61B 1/07 (2013.01); G02B 23/2469 (2013.01); G06T 5/003 (2013.01); G06T 2207/10064 (2013.01); G06T 2207/10068 (2013.01); G06T 2207/30096 (2013.01)

(58) Field of Classification Search
CPC .............................. A61B 1/00165; G06T 5/50
See application file for complete search history.

Primary Examiner — Jason M Ip
(74) Attorney, Agent, or Firm — Osha Bergman Watanabe & Burton LLP (57) ABSTRACT

A high-resolution microendoscope system includes a light source, a fiber optic bundle configured to transmit light from the light source to a sample, a disc configured to receive light returned from the sample, the disc having spaced apart segments, the spaced-apart segments being at least one of openings and transparent portions, a first camera configured to capture a first image based at least in part on light passing through the disc, and a second camera configured to capture a second image based at least in part on light reflected from the disc.

20 Claims, 7 Drawing Sheets

Figure 10

HIGH RESOLUTION MICROENDOSCOPE EMPLOYING DIFFERENTIAL STRUCTURED ILLUMINATION AND METHOD OF USING SAME

CROSS-REFERENCE TO RELATED APPLICATION

The present application is a continuation application of U.S. patent application Ser. No. 15/957,442, filed Apr. 19, 2018, which is a continuation application of International Application No. PCT/US16/57599, filed Oct. 19, 2016, which claims priority to U.S. Provisional Application No. 62/243,323, filed on Oct. 19, 2015 and titled "Differential Spinning Disc-High Resolution Microscope," which are hereby incorporated by reference herein in their entirety.

STATEMENT REGARDING FEDERALLY SPONSORED RESEARCH OR DEVELOPMENT

This invention was made with government support under Grant Number R01CA140257 awarded by the National Institutes of Health. The government has certain rights in the invention.

SUMMARY

The present disclosure relates generally to improving image quality in a high resolution microendoscope (HRME). An HRME, which is considered an epifluorescent microendoscope imaging system, is an imaging device that uses a small, flexible, fiber-optic bundle to scan across tissue of a patient to analyze nuclear morphology and identify areas of cancer. An HRME is generally portable and can be easily carried by a user. The present disclosure includes a method to add optical sectioning to an HRME to subtract background light in order to improve the image quality of the device.

More particularly, an HRME is an imaging system that uses a fiber-bundle probe to image fluorescent samples. In operation, light travels to and from a sample (e.g., tissue) via the fiber-bundle probe and is imaged onto a charge-coupled device (CCD) camera. Fiber bundles lack inherent optical sectioning (e.g., background light removal) capabilities without modification. Koucky M. H., Pierce M. C., "Axial response of high-resolution microendoscopy in scattering media," Biomed. Opt. Express 4(10), 2247-2256 (2013). This frequently causes the HRME to have poor image contrast when imaging highly scattering tissue.

A known optical sectioning technique for microscopy is referred to as structured illumination (SI). A method of obtaining optical sectioning by using structured light in a conventional microscope, as shown by Bozinovic, N., Ventalon, C., Ford, T., & Mertz, J. in "Fluorescence endomicroscopy with structured illumination," Opt. Express, 16(11), 4603-4610 (2008), is capable of rejecting background light in a fiber-bundle based microendoscope system. However, Bozinovic's method requires three sequential frames to be combined to form one single optically sectioned (background removed) image. A problem with such a requirement is that any motion (on the micrometer level) while acquiring these three images will cause artifacts and render the single optically sectioned image unintelligible.

The invention of one embodiment of the present disclosure eliminates the need to acquire three images, meaning no artifacts, which enables in vivo (i.e., in the body) use and/or other applications requiring video rate acquisition of a moving sample. In one embodiment, the presently disclosed technology implements SI using a spinning disc with a reflective grating to modulate the excitation and emission pathways. The portion of the emission light returning from the fiber-bundle that transmits through the grating can be imaged onto a CCD camera. This image can be the widefield image. The wide-field image is a normal image taken by the HRME that has not been optically sectioned (background removed). The portion of the light which strikes the reflective grating emanates from the background of the sample being imaged. This is reflected onto a second CCD camera, thereby resulting in an image containing the light emanating from the background of the sample. Subtracting the two images (wide-field minus background image) results in a sectioned image. Both images can be recorded simultaneously. One embodiment of the system of the present disclosure is called a Differential Structured Illumination Microendoscope (DSIMe).

The features and advantages of the present disclosure will be readily apparent to those skilled in the art upon a reading of the description of the embodiments that follows.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Figure 2:
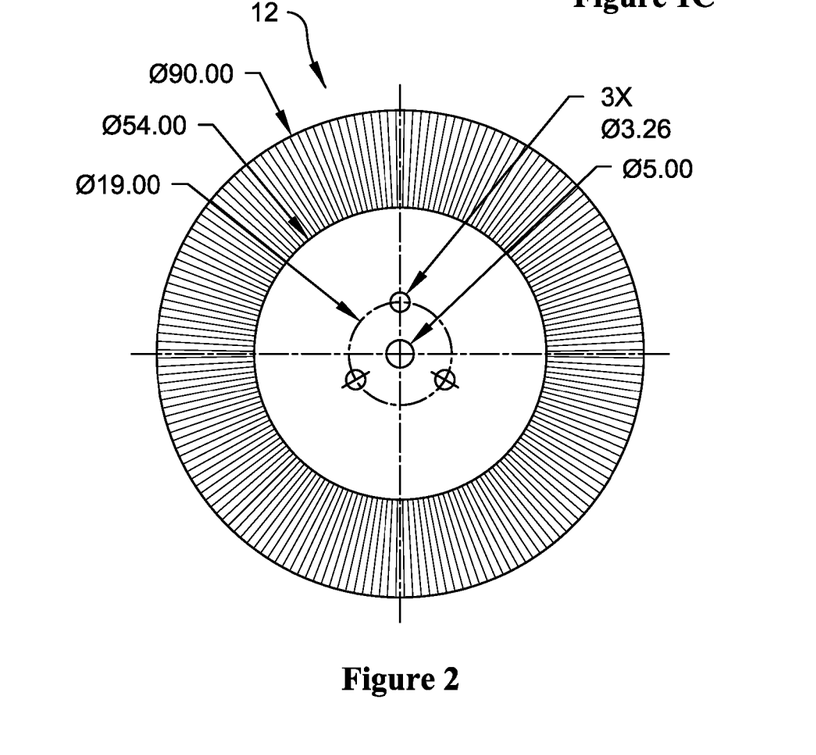
FIG. 2 is a schematic diagram of a portion of the system shown in FIG. 1A.

In one embodiment, the system of the present disclosure is configured to perform background subtraction to improve HRME image quality. The system, generally designated 10, can utilize a spinning disc, generally designated 12, or other object. In one embodiment, at least a first portion of the spinning disc 12 can be reflective, and at least a second portion of the spinning disc can include spaced-apart openings or grating. As shown in FIG. 2, the disc 12 can include spaced-apart and elongated slots extending radially outwardly from a geometric center of the disc 12. Alternating slots can be open or extend through the disc 12, while slots in between the alternative openings can be formed of a reflective material. This reflective spinning disc grating (sometimes referred to as a "rotating grating") is configured to receive, capture and/or measure the background light from a standard HRME image. In one embodiment, a first portion of the spinning disc can be at least substantially transparent (e.g., to replace the spaced apart openings), while the second region can be reflective. One embodiment of the disc is shown in FIG. 2. The disc 12 can be mounted to a motor 22, such as a spinning stepper motor. Once the background light is acquired by a CCD camera, for example, the background can be subtracted from a standard HRME image (e.g., a widefield image).

Figure 1A:
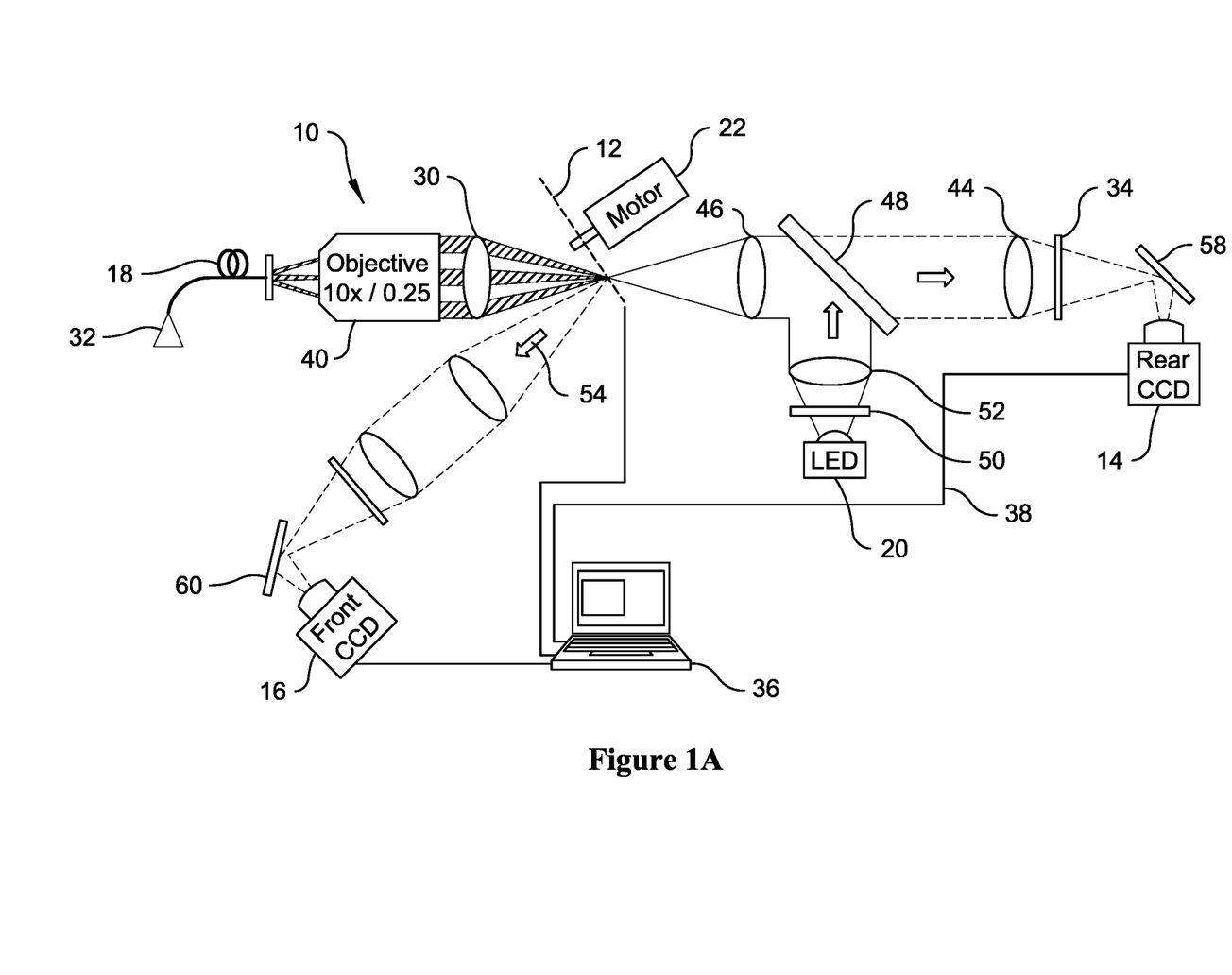
FIG. 1A is a schematic diagram of a system of one embodiment of the present disclosure.

The DSIMe can include a light source 22, a fiber-optic bundle 18, a microscope objective lens 40, an achromatic lens 30 that can be separate and spaced-apart from the objective lens 40, and a first or rear CCD camera 14. In operation, background can be reflected in a second or front camera 16. A widefield image can be recorded in the first or rear CCD camera 14. The disc 12 can be spun quickly relative to the exposure time of the camera(s) to average out the modulation in both images.

The DSIMe can perform optical sectioning at video rate without suffering motion artifact. In one embodiment, the system of the present disclosure does not require any optics or scanning mechanism at the distal end of the fiber bundle, making it ideal for in vivo use. In other words, all of the optical components can be located on the proximal side of the fiber bundle, which facilitates small probes for in vivo imaging. In another embodiment, the DSIMe could be used in conjunction with fiber bundles that have additional optics attached at the distal tip of the fiber bundle to improve spatial resolution and provide sub-surface imaging.

The axial response of the system has been quantified using an optical phantom and show that improved optical sectioning results in improved image contrast in an ex vivo animal model. A clinical pilot study was then performed to demonstrate in vivo imaging in patients undergoing surgical treatment with conization for cervical adenocarcinoma in situ (AIS). The results demonstrate contrast enhancement and improved ability to detect the cellular atypia associated with neoplasia in real time.

For imaging, a fluorescent contrast agent or an object or body that is autofluoresent can be applied to the sample (e.g., tissue), and the distal tip of the bundle can be placed in direct contact with the sample, thereby delivering excitation light. Fluorescence emission from the sample 32 can be collected by the bundle 18. Light emanating from background regions can be imaged onto the second CCD camera 16 after it strikes the reflective grating of the disc 12. In one embodiment, light emanating from the focal plane can transmit through and/or between the gratings of the disc 12, a dichroic mirror 48 and/or an emission filter 34, before being imaged onto the first CCD camera 14 by a tube lens 44. A conventional or normal mirror 58 also may be positioned in the path between the emission filter 34 and the first camera 14. The focal length of the tube lens can be chosen such that the image fills the CCD sensor and the Nyquist sampling criterion is satisfied. Images can be transferred from the first camera 14 to a computer device 36, such as a laptop, via a wired or wireless connection 38, such as a USB 3.0 cable, for real-time display and subsequent analysis. Images can be transferred from the second camera 16 to the computer device 36 in a similar or different manner. Likewise, the computer device 36 can be operatively connected to the disc 12 and/or the motor 22 in a similar or different manner.

Figures 1B, 1C:
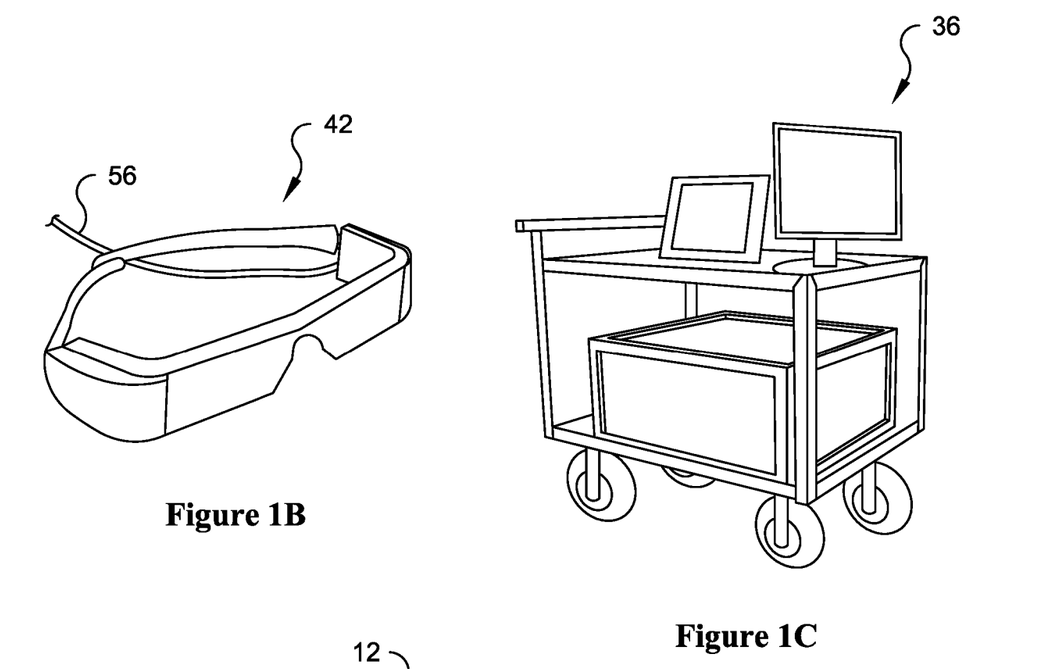
FIG. 1B shows a smart glasses system of one embodiment of the present disclosure.
FIG. 1C shows an optical enclosure and computer system of one embodiment of the present disclosure.

In at least certain embodiments, as shown in FIGS. 1-2, unique features or components of the DSIMe system are at least the inclusion of the disc grating 12, the second or front CCD camera 16, and several additional lenses. In operation, the second CCD camera 16 is configured to record the background light reflecting off of the disc grating 12. The first CCD camera 14 is configured to record the standard HRME. The images obtained from both cameras 14, 16 can be recorded simultaneously, or the images can be recorded at separate times or in sequence. In one embodiment, the software is configured to subtract the two images automatically, and can display the results to a user.

In one embodiment, the DSIMe system is designed to offer a portable platform to perform in vivo imaging in an operating room or clinic setting. A high power LED 20 can provide illumination and a spinning reflective grating 12 can modulate the illumination pathway, which can be imaged onto a coherent fiber optic bundle (e.g., a fiberscope) 18 placed in contact with the tissue surface. Modulated excitation light can be relayed to the sample (e.g., tissue) by the fiber bundle 18. Corresponding modulated emission light can return via the same optical path and can be imaged onto the reflective disc grating 12 via an objective 40 and a relay lens 30. Light emanating from in-focus and out-of-focus optical planes of the fiber bundle 18 can pass through the grating 12 unobstructed and can imaged by a tube lens onto the rear CCD camera, resulting in a widefield image. Light from optical planes past the defocus point of the grating image on the fiber bundle 18 can strike the reflective grating 12 and thereby can be reflected towards a second optical pathway 54. This out-of-focus background light can be imaged onto the front CCD camera, through one or more spaced-apart lenses before passing through an emission filter and reflecting off of a mirror 60. A depth of the defocus point in SI imaging can depend on the grating modulation frequency. The grating 12 can be rotated rapidly relative to the exposure time of the CCD cameras to average out the modulation in both images. Proper spatial co-registration can be maintained through the use of a real-time image stabilization algorithm. Images can be displayed via computer monitor or wirelessly relayed to a pair of smart glasses 42 (see FIG. 1B). The smart glass interface 42 can be used to relay images directly to clinicians during in vivo operation of the device. This feature allows clinicians using the DSIMe to simultaneously watch where they are placing the fiber bundle during imaging and see images and instrument status.

More particularly, FIG. 1A shows the optical layout of a DSIMe system according to one embodiment of the present disclosure. A high power LED 20 can emit approximately or exactly 455 nm light, which can pass through an excitation filter 50 and can be collimated by a collection lens 52. The excitation light can pass through a relay lens, can reflect off a dichroic beam splitter 48, and can illuminate the disc grating. The grating can rotate continuously during imaging to average out the grating pattern in the final images. The modulated excitation light can be imaged via a second relay lens 30 onto the rear of the objective. A fiber optic bundle 18 can be comprised of 30,000 individual fibers can be placed at the objective's working distance. Modulated excitation light can be relayed to the sample by the fiber bundle. Corresponding modulated emission light can return via the same path. The returning modulated fluorescence emission can be imaged onto the reflective disc grating via the objective and the same relay lens. Light emanating from in-focus and out-of-focus optical planes of the fiber bundle can pass through the grating unobstructed and is imaged by a tube lens onto the rear CCD camera 14, resulting in a widefield image. Light from optical planes past the defocus point of the grating can strike the reflective grating and can be reflected towards a second optical pathway. This out-of-focus background light can be imaged onto or by the second CCD camera 16. The depth of the defocus point in SI imaging can depend on the grating modulation frequency. Both CCD cameras can be triggered simultaneously to acquire the widefield and background images. Subtracting the background image (e.g., the front CCD camera 16) from the widefield image (e.g., the rear CCD camera 14) yields an optically sectioned image. A multiplier can be applied to the background image to account for differences in throughput between the front and rear optical pathways. The widefield image can be compared to the subtracted sectioned image for immediate comparison between standard widefield high resolution microendoscopy and DSIMe.

For subtraction of the widefield and background images to accurately remove out-of-focus light, it is necessary to maintain proper spatial image co-registration between the two images. Building a motorized rotating disc grating that can remain steady at the micron scale is challenging and would require expensive and precisely machined components. As a low-cost, practical alternative, the presently disclosed technology includes an image stabilization routine to properly co-register the two images in real-time. A one-time calibration routine during system startup can rotate the disc through one revolution in incremental steps. At each angular position of the grating, the location of the image of the fiber optic bundle can be identified on the front CCD camera. As described in more detail below, a look-up table can then be constructed correlating the angular position of the grating to the location of the fiber bundle image. During DSIMe operation in one embodiment, the control software can record the angular position of the grating when triggering image acquisition. Using the look-up table, an algorithm can register the images, correcting for xy-displacement of the fiber bundle caused by any periodic motion in the rotating disc prior to image subtraction. Correction can occur in real-time and the system can acquire sectioned images at frame rates up to 12 frames per second (fps) depending on exposure time. Images can be displayed via computer monitor or wired 56 or wirelessly relayed to a pair of smart glasses (FIG. 1B). The smart glass interface can be used to relay images directly to clinicians during in vivo operation of the device.

The DSIMe system 10 of the present disclosure may include one or more (e.g., four) USB cables, a footswitch, a control box, LED power supplies and/or a power strip, in addition to the components described above. In operation and prior to use of one embodiment of the DSIMe, the motor, footswitch and camera USB cables should be connected to the laptop. Next, the fiber-optic probe bundle 18 can be connected to the microscope. Next, the power strip connected to the microscope can be turned "ON". In one embodiment, a blue light can be emitted through the fiber to indicate power has been supplied.

In one embodiment, motor stability is critical for successful image co-registration. Movement on the order of microns may mean that the image recorded by the second camera 16 is constantly moving. If the wide-field image and background are not spatially co-registrated correctly, then the background subtraction may not function properly. A software and/or mechanical solution can be developed to record where the image is located versus the position of the motor using the motors position tracking, image processing, and the fiber-bundle. With this information, the differential spinning disc (DSD) software can keep the image centered by applying an xy-shift to the image position in real-time. The amount that the DSD software needs to shift the image can be based on a calibration routine that is performed on system start-up, which records image position versus angular position of the motor.

In one embodiment, a calibration routine can be performed. The motor can be instructed to begin stepping through 360 degrees of rotation. In one embodiment, there are 100 steps (3.6 degrees per step). At each step, the angular position of the motor along with the x,y image position can be recorded to form a look-up table, such as that shown below and in FIG. 3.

TABLE 1

Figure 3:
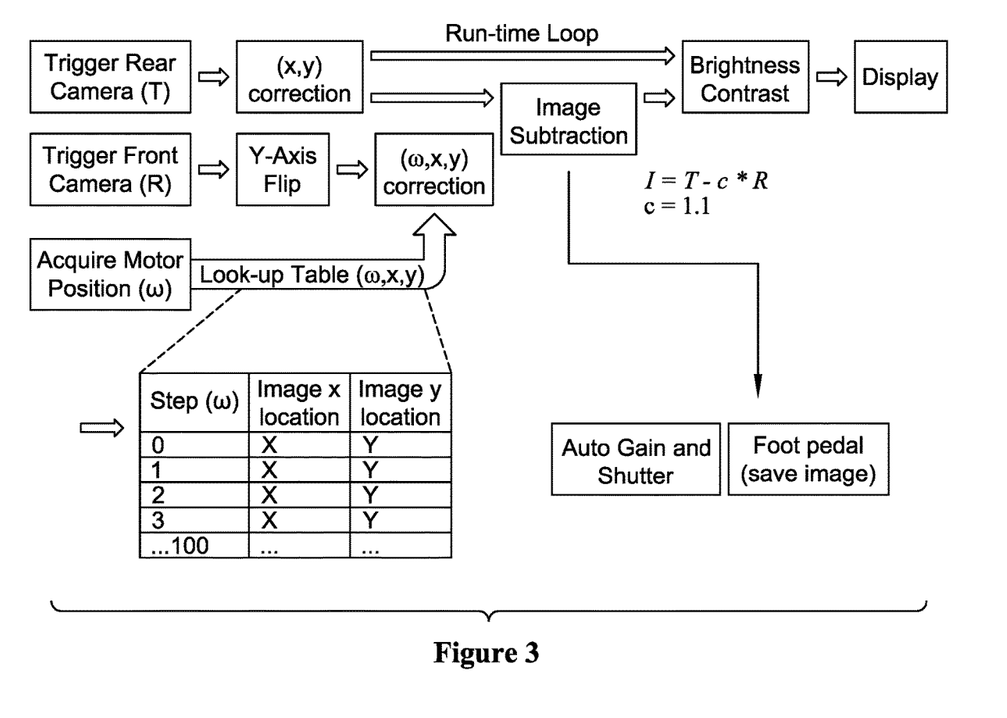
FIG. 3 is a flow diagram of a method of operation of a device of one embodiment of the present disclosure.

| Step (motor position) | Image x pixel location | Image y pixel location |
| --- | --- | --- |
| 0 | $X_0$ | $Y_0$ |
| 1 | $X_1$ | $Y_1$ |
| 2 | $X_2$ | $Y_2$ |
| 3 | $X_3$ | $Y_3$ |
| ... 100 | ... | ... |

The image location can be found using an image processing algorithm based around the shape of the fiber-bundle. The fiber-bundle 18 can be a round object. A circular edge filter has been developed to find the exact location of the fiber-bundle in each image. Once the circle was found, the center position in pixels was recorded (x, y). The change in this location step-to-step correlates to the offset needed to keep the image stable as the motor spins. In operation, in one embodiment, blue lines can be line scans looking for the best dark-to-bright edge starting from the outside (lateral) and moving toward a center of the image. The line scans form a radial pattern and coverage at the center of the image. The location of the best edge in each line can be found and a circular fit can be made (e.g., red line). The center of the circle (e.g., red dot, center of image) can give the x-y location recorded in Table 1. Once the motor has stepped through all 100 steps (i.e., 360 degrees of rotation), the system 10 can know the image location of the fiber-bundle based on the angular position of the motor.

Once the system 10 is calibrated, the motor can be set to rotate at a constant speed. The system can then trigger both cameras 14, 16 to acquire images simultaneously, such as shown in FIG. 3. An x,y correction to the transmission image (rear or first camera 14) can be applied to center the image. This image can be unaffected by the spinning disc as it passes through the disc grating and is not destabilized. In one embodiment, the reflected image (front or second camera 16) must be centered using the look-up table (e.g., Table 1) from the calibration routine. First, the motor location is found (acquired at the same time both cameras begin acquiring an image). Using the motor location, the x,y correction acquired during calibration needed to center the image is found and then applied to the image. Now that both transmission (rear) and reflected (front) images have been centered, they are now properly co-registered. A subtraction is performed and the result is a sectioned imaged that is displayed to the user.

Additionally, in one embodiment, there is a delay between when the program queries the motor for its location and when the motor responds. During this time, the motor can still be rotating, meaning that the location it sends to the DSD software may no longer precisely correlate to the correct image location being acquired by the camera. To account for this, a step offset can be added to account for delay. For example, if the motor returns its angular position as "step 56," but the delay is known to correlate to a 2-step error (meaning the motor was actually at "step 58" when the image was acquired), the index offset will add two (2) to correct for the delay and shift the image based on the x,y location correlated to "step 58", not "step 56". This was found to increase the effectiveness of the stabilization and correct for run-time delays. This step offset can be found by measuring the response time of the motor system and using the rotation speed of the motor to determine the correct offset.

Figure 4:
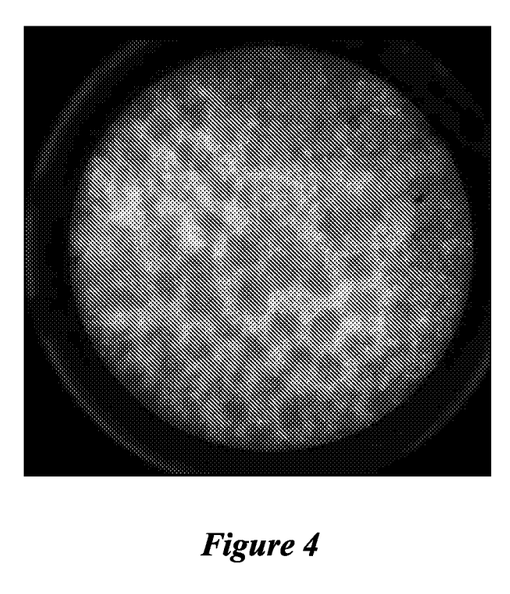
FIG. 4 is an image of animal tissue acquired using conventional HRME technology.
Figure 5:
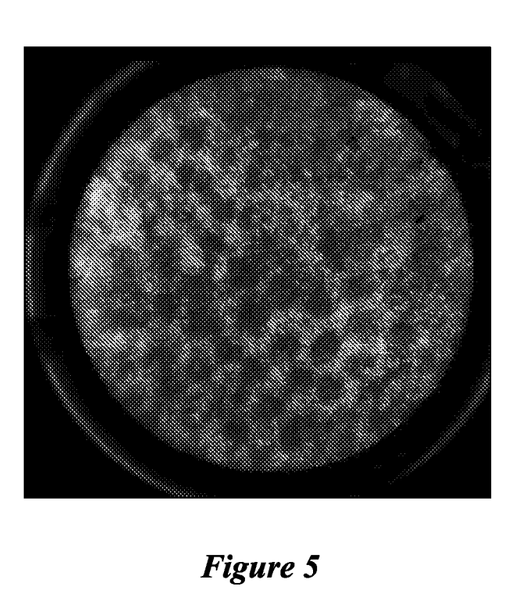
FIG. 5 is an image of animal tissue acquired using DSIMe technology of one embodiment of the present disclosure.

Performance testing has been conducted in animal tissue to evaluate the background subtraction capabilities and functionality of the system. As shown in FIG. 4, an image of mouse stomach tissue was acquired using conventional HRME without background subtraction. As shown in FIG. 5, an image of the same tissue was acquired using the DSIMe of the present disclosure with background subtraction and successful image co-registration. FIGS. 4 and 5 are from the same field-of-view. Glands are visible in both images, but contrast is visibly improved using the DSIMe of the present disclosure, thereby making nuclear morphology more easily discernable.

A device of the present disclosure implements SI in a microendoscope without suffering from motion artifacts and facilitates in vivo imaging. In one embodiment, the device 10 (see FIG. 1) of the present disclosure can be used to image human tissue in vivo to screen for pre-cancer. There are many sources of motion when imaging tissue in vivo (e.g., a doctor's hand, patient motion, patient breathing, tissue malleability, etc.). The device 10 of the present disclosure will make using this SI technique possible since it does not suffer from motion artifacts like previous implementations of SI in a microendoscope. The standard HRME system has been used in many clinical trials successfully to identifying pre-cancers lesions. Muldoon T. J., Pierce M. C., Nida D. L., Williams M. D., Gillenwater A, Richards-Kortum R., "Subcellularresolution molecular imaging within living tissue by fiber microendoscopy," Opt. Express 15(25), 16413-16423 (2007). The DSIMe of the present disclosures improves the image quality of the HRME, particularly in tissue that the standard HRME has struggled with imaging due to poor image quality.

In one embodiment, excitation light from an LED 20 can be collimated by an achromatic lens before being reflecting by a dichroic beamsplitter. The light can then be imaged onto the reflective spinning disc grating 12 by a relay lens before being imaged onto the back aperture of an objective. The fiber-bundle 18 can then be placed at the working distance of the objective and the grating 12 is imaged onto the fiber 18. Cores residing in an area blocked the grating transmit no light to the sample whereas cores residing in areas where light passed unobstructed through the grating transmit the excitation light to the sample. Excitation light emanating from the unblocked cores excites fluorophores in the sample. Fluorescence emanating from all optical planes return via the unblocked cores. Fluorescence emanating from beyond the defocus point of the grating image 12 and scattered light from excited areas enters the cores initially blocked by the grating. The depth of the defocus point if the grating image can be adjusted based on the frequency of the introduced modulation. The fluorescent can then return to the objective and can be imaged by the relay onto the grating. Light from the unblocked cores again transmits through the grating 12 and can be imaged onto a CCD forming a wide-field image (unsectioned image). The fluorescence returning from the initially blocked cores can be reflected by the grating and imaged onto a second CCD (background image). This image can contain out-of-focus light and when subtracted from the wide-field image results in a sectioned image.

In an alternative embodiment, the grating pattern and frequency on the disc can be changed to optimize background subtraction. In addition, optical focal lengths of the lens in the system can be optimized to reduce size, cost and complexity.

The DSIMe can be used to acquire image data from tissue following application of proflavine solution (0.01% w/v) as a fluorescent contrast agent. In one embodiment, prior to imaging, the system or device must be calibrated. To do so, a calibration standard can be attached to the fiber connector. Once calibration is finished the standard can be removed and imaging can begin. For optimal image quality, the fiber-optic bundle should be focused in the system. This should be checked before each imaging session by confirming that individual fibers in the bundle can be distinguished on-screen. The focus can be adjusted by turning a focus-adjust wheel, for example, inside the system or device.

In one embodiment, the fiber-optic probes can be made of glass and should be handled carefully. The fiber may break if subjected to tight bending (radius<40 mm) Retroflexing within an endoscope should be avoided. The fiber optic probe should be thoroughly cleaned and the probe should also be disinfected with a high level disinfectant prior to first use. More particularly, the fiber-optic probe should be cleaned thoroughly with an enzymatic detergent, such as Enzol, with a disposable cloth/sponge prior to and after use with each patient. This process should be conducted immediately before high level disinfection.

In one embodiment, to begin the cleaning process, the enzymatic detergent can be applied to a disposable cloth/sponge the probe can be thoroughly wiped-down, focusing on the tip. After cleaning the probe, it should be thoroughly rinsed to ensure there are no residual organic or inorganic materials present. The probe should then be wiped dry with paper towels or lap pads prior to high level disinfection. It may be important to ensure there is no biological material on the probe, including the tip of the probe and repeat this process if necessary.

The end faces of the fiber-optic probe can be easily chipped and/or scratched on contact with hard or rough surfaces. Therefore, prior to using the probe, one should ensure there are no obvious cracks in the distal tip of the fiber and that the epoxy ball is intact. The epoxy ball is added to the distal tip of the fiber-bundles to increase surface and provide a rounded edge, so the fiber-bundle will not catch on folds in malleable tissue. This facilitates smooth scanning of the probe across the surface of tissue. Additionally, after starting the system, one should verify that the image is clear of any debris by pointing the fiber at a distant object and ensuring the visual field remains clear. If there is any visible debris on either end face, the debris can be removed by gently cleaning the end faces with optical lens paper and isopropanol (IPA). In cases where the probe has been inappropriately handled and the face is scratched, the probe tip can be polished until a clear image is achieved.

A prototype of the DSIMe has been built, and is physically larger than a conventional HRME, which is about the size of a shoebox. The prototype of the DSIMe includes an optical 36×24" breadboard, which can be easily transported via a cart. The conventional HRME system has gone through several miniaturization design phases, and it is expected the DSIMe could also be reduced in size and complexity in a similar design cycle. One application for the prototype is an in vivo cervical cancer screening of a patient.

Fiber-bundles introduce additional complications that do not exist in "traditional" microscopy. First, one must account for how the fiber-bundle samples grating. In structured illumination microscopy (SIM), one can increase/decrease the frequency of the grating pattern to increase/decrease the sectioning strength of the system. The frequency limitations of the grating in "standard DSD" are dependent on the resolving limit of the lens, objective, and CCD camera. When introducing a fiber-bundle, each core acts as a pixel, this becomes the limiting factor of the resolution of the system (dependent on size and spacing of each core). One cannot use a grating frequency that corresponds to a width smaller than a single fiber-core.

Second, while the sectioning strength of the system is ultimately dependent on frequency of the grating, one also has to account for the numerical aperture (NA) of the fibercores when quantifying optical sectioning strength. Fiber-bundles of different size, shape, and material will have varying NA. The sectioning strength will still vary with frequency of the grating, but a change in grating frequency will not result in the same change in sectioning strength in a fiber based system compared to microscopy since the optical transfer function of the fiber-bundle must be accounted for. Also, with standard microscopy the objective can focus through a 3D volume whereas in a fiber-based system the objective is imaging the light returning from a single 2D focal plane (fiber-bundle).

In contrast to the presently disclosed technology, the invention disclosed in International Patent Application Publication No. WO 2007/022196 A2 produces an undesirably low signal to noise ratio in highly scattering tissue. Such a deficiency has necessitated, at least in part, the need for a device which can perform background rejection in real-time for in vivo and/or ex vivo tissue imaging, which is achievable by the system of the present disclosure. Confocal techniques have been developed in the past to provide optical sectioning to fiber-bundle based imaging systems, but many cannot be performed in real-time or require complex optics to be attached to the distal end of the fiber-bundle. Additional complex optics at the end of the fiber-bundle can make in vivo imaging mechanically impossible. The addition of a fiber-bundle is a non-trivial problem to overcome when attempting to perform confocal imaging. The DSIMe of the present disclosure does not require additional optics and imaging with optical sectioning can be performed in real-time at video rates.

International Patent Application Publication No. WO 97/31282 A2 (Wilson) discloses optical sectioning in real-time. However, such work makes no mention of fiber-optic imaging. Confocal techniques, like that disclosed in Wilson, developed for standard microscopy often do not work for fiber-bundle imaging without additional optical systems on the distal-tip of the fiber-bundle or a scanning mechanism (see Flusberg below). These additions for performing optical sectioning in a fiber-based system often make in vivo imaging mechanically impossible. Techniques that can provide optical sectioning without compromising the flexibility and size of the probe are challenging and not obvious to develop. Given the technical challenges previously encountered with developing a fiber microendoscpe capable of performing optical sectioning and imaging in vivo at video rates, the presently disclosed technology is both novel and non-obvious. See Flusberg, B. a, Cocker, E. D., Piyawattanametha, W., Jung, J. C., Cheung, E. L. M., & Schnitzer, M. J. (2005), titled "Fiber-optic fluorescence imaging," Nature Methods, 2(12), 941-950.

In addition, a practical problem when developing the spinning disc system with multiple imaging devices of the present disclosure was ensuring proper spatial image coregistration. The technique disclosed herein utilizes the fiber-bundle image as a means to stabilize the image in real-time. Wilson (i.e., WO 97/31282 A2) provides no disclosure regarding stabilization or how to ensure their two images are co-registered successfully. Wilson states, "[the two camera] arrangement introduces greater difficulties with alignment as compared with the two light source system." Wilson acknowledges the problem, but offers no mention of a solution. The two light source system referenced by Wilson requires two images to be captured in sequence which would likely suffer from motion artifacts similar to previously discussed embodiments. The device of the present disclosure has solved this problem. The technique disclosed herein specifically uses the fiber-bundle to achieve stable co-registration in real-time at video rates.

To demonstrate the performance of axial sectioning using the DSIMe, a solution containing fluorescent 15 µm microspheres were pipetted or deposited onto a clear glass microscope slide. After the microspheres were deposited onto the glass slide, the solution was allowed to dry and then the slide was placed in contact with and slowly (e.g., incrementally) stepped away from the fiber bundle. This process was performed three times: once for widefield imaging with the reflective grating removed, and then with two discs with different grating frequencies of 9 lpm and 25 lpm. LED power was increased when the disc was removed so the average intensity at the start of each measurement was equal. The disc was removed for widefield imaging, so a comparison could be made between standard epi-flourosecent microendoscopy and DSIMe. The average in intensity for each was measured and analyzed using ImageJ (NIH ver 1.47v).

Figure 6:
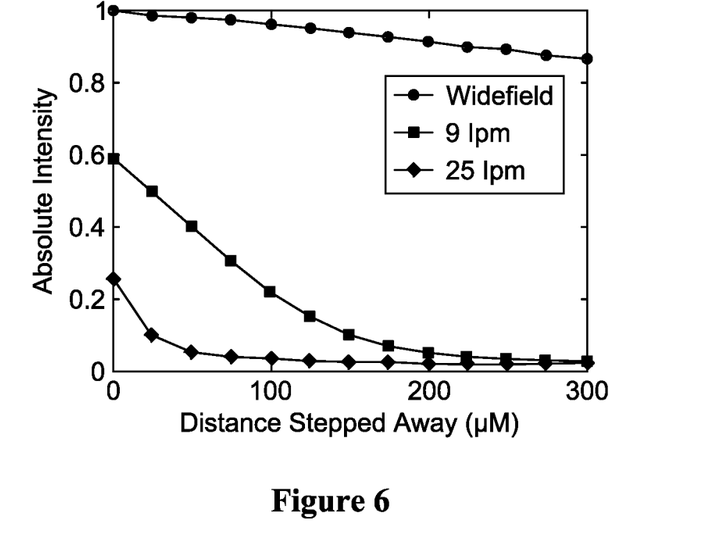
FIG. 6 is a graph charting quantified sphere intensity normalized vs. distance from the tip of a fiber bundle to a sample for widefield images, DSIMe images at 9 lines per millimeter (lpm) modulated frequency, and DSIMe images at 25 lpm modulated frequency.
Figure 7:
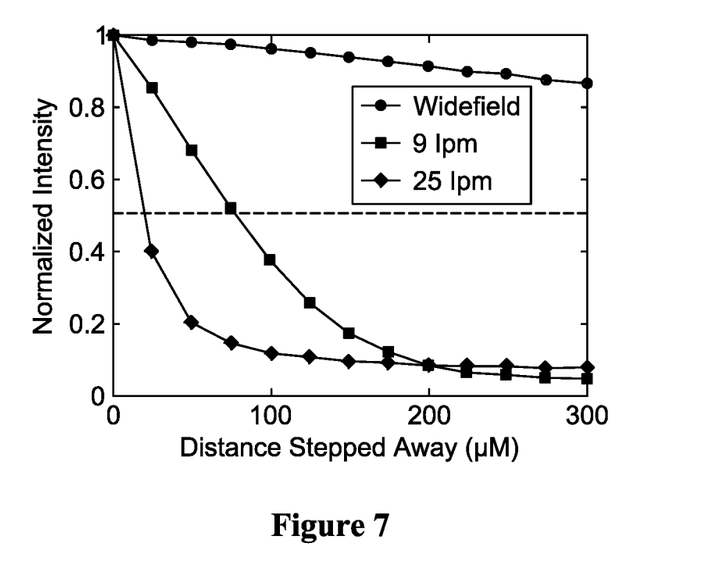
FIG. 7 is a graph charting quantified sphere intensity absolute vs. distance from the tip of a fiber bundle to a sample for widefield images, DSIMe images at 9 lpm modulated frequency, and DSIMe images at 25 lpm modulated frequency.

FIGS. 6 and 7 chart data of the fluorescent microspheres at different distances from the distal tip of the fiber bundle. In conventional widefield images microspheres are clearly visible at distances up to 100 µm with increased size due to defocus. In contrast, DSIMe images show improved optical sectioning as the frequency of modulation is increased. Using a grating with 9 lpm, microspheres are no longer visible at a distance of 100 µm. At 25 lpm, microspheres in DSIMe images are no longer visible at a distance of 50 µm. Average sphere intensity vs. distance is quantified in FIG. 6. Without SI, the average intensity changes minimally with increasing distance between the sample and the distal tip of the fiber bundle. With SI, the intensity attenuates more rapidly as the distance between the sample and the distal tip of the fiber bundle increases, illustrating the optical sectioning capability of DSIMe. Microsphere intensity at 9 lpm reaches 50% initial intensity at approximately 75 µm. At 25 lpm microsphere intensity reaches 50% initial intensity at sub-25 µm. Measuring microsphere intensity attenuation with respect to distance demonstrates a modulation frequency dependence on axial sectioning strength. However, as shown in FIG. 7, more in-focus light is lost at higher modulation frequencies. Infocus signal attenuation was approximately 40% at 9 lpm and 75% for 25 lpm illustrating the trade-offs between sectioning and signal. Increasing the modulation frequency to increase sectioning strength comes at the expense of signal loss at higher modulation frequencies, which has been observed in previous work using SI in microendoscopes.

To determine if the improved axial sectioning capabilities of DSIMe observed with the microsphere phantom in air would translate to contrast enhancement in highly scattering tissue, excised mouse stomach and colon were imaged ex vivo. Proflavine (0.01% w/v in sterile PBS), a fluorescent contrast agent which stains cell nuclei, was topically applied to mouse stomach and colon and imaged immediately. The mouse tissue was obtained from female C57/BL6J mice 12-16 weeks of age. All mouse experiments were performed in accordance with an Institutional Animal Care and Use Committee approved protocol at Rice University. Imaging was performed with the 9 lpm disc grating. The fiber optic bundle was placed in gentle contact with the mucosa and scanned across the tissue surface. To compare signal and background intensity in DSIMe and widefield images, line scans were plotted from the same location in widefield and DSIMe images. To remove the fixed pattern associated with the fiber bundle, a fiber core removal algorithm was used. In brief, the algorithm interpolates the pixel intensity of the fiber cladding based on the pixel intensities within the fiber core. The intensity value of the center pixel is then used to assign all non-center pixels the same intensity value to the nearest center pixel; giving the cladding the same pixel intensity as the core. Core removal and lines scans were performed on raw widefield and DSIMe images prior to any contrast or brightness adjustments enhancement. The core removal algorithm and line scans were performed in post processing using a Matlab script and ImageJ respectively.

Figure 8:
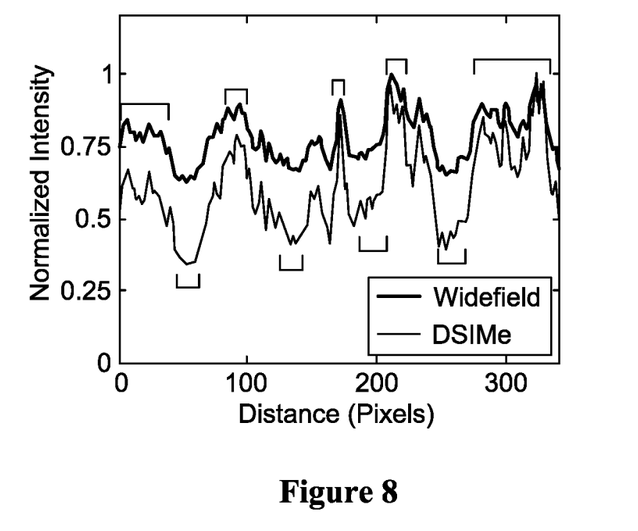
FIG. 8 is a graph of line scans of a mouse stomach comparing a widefield image and a DSIMe image.
Figure 9:
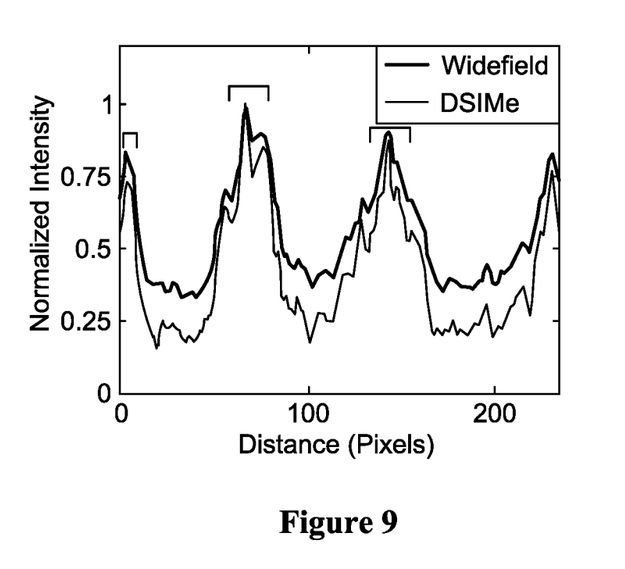
FIG. 9 is a graph of line scans of a mouse colon comparing a widefield image and a DSIMe image.

FIGS. 8 and 9 chart data from widefield and DSIMe images of excised mouse tissue. Use of DSIMe was found to visibly improve contrast in images of mouse colon and stomach. DSIMe signal from the line scans used in FIGS. 8 and 9 show improved contrast between glandular wall and lumen compared to widefield images. The average normalized intensity for the gland walls (maxima) was compared to the average intensity of the lumen (minima) indicated by the brackets. The ratio of the average maxima to minima increased in the DSIMe image of colon by 32% ($1.27 \pm 0.05$ for widefield to $1.7 \pm 0.2$ for DSIMe) shown in FIG. 8. In stomach, shown in FIG. 9, the ratio increased by 46% ($1.9 \pm 0.2$ to $2.8 \pm 0.6$) when comparing the widefield to DSIMe image. The use of DSIMe imaging resulted in higher contrast images in both tissue types.

To demonstrate clinical utility of the DSIMe device, cervical tissue was imaged in vivo in patients undergoing surgical treatment with conization for AIS. Prior to imaging, proflavine was topically applied to the cervix. The fiber bundle probe tip was placed in contact with visually normal and abnormal areas and widefield and DSIMe images were obtained by the clinician. All images were displayed in real-time via computer monitor or smart glass system. Representative widefield and DSIMe images of normal and neoplastic tissue were produced. All images showed an abrupt transition from a region of normal squamous epithelium to a region of high grade squamous intraepithelial lesion (HSIL). Normal squamous epithelium is characterized by regularly spaced, small nuclei. In contrast, the images of HSIL showed larger, more closely spaced nuclei. This is consistent with previous studies using high-resolution microendoscopy to study squamous epithelium where increased nuclear density and nuclear size are observed in dysplastic tissue. The DSIMe images corresponding to the HSIL region show improved image contrast. Contrast enhancement was observed in the DSIMe image facilitating visualization of nuclear morphometry. Contrast was improved in the DSIMe image facilitating imaging of epithelial cell nuclei.

As demonstrated in the optical phantom, sectioning strength varies with modulation frequency. Increasing the modulation frequency to increase sectioning strength comes at the expense of signal loss at higher modulation frequencies, which has been discussed in previous work using SI in microendoscopes. Despite this loss, DSIMe images of scattering mouse and human tissue show higher image contrast in comparison to widefield microendoscopy. Improvements in image contrast enable improved recognition of nuclear morphometry particularly in areas of precancer and cancer. While visually compelling, the improved nuclear recognition could also improve automated algorithms designed to identify neoplasia in real-time that would otherwise struggle in highly-scattering tissue. Additionally, since DSIMe maintains the small size of the probe, this technique could be used to improve high resolution microendoscopy imaging in a wider array of tissues. Other studies using high-resolution microendoscopy have been conducted to study esophageal, liver and pancreas, colon, and oral cancers. The fiber probe is small enough to fit into the biopsy channel of a standard endoscope allowing it to be used in conjunction with current endoscopy. Differential structured illumination microendoscopy offers a promising technique to improve image contrast in realtime without motion artifacts or the need to sacrifice miniaturization of the probe which better facilitates in vivo imaging of tissue in conjunction with molecular contrast agents.

The optical performance of the DSIMe system using a reflective grating of 9 lpm was evaluated in an IRB-approved pilot study of patients undergoing cold knife cone (CKC) treatment for diagnosed AIS. Patients gave informed consent and the study was reviewed and approved by the IRBs at Rice University and University of Texas MD Anderson Cancer Center. Five patients out of twenty total enrollment have been imaged. Prior to imaging, proflavine hemisulfate (0.01% w/v in sterile phosphate buffered saline) and Lugol's Iodine were topically applied to the cervix. Following application of proflavine, the DSIMe probe was advanced through the speculum and used to image the cervix. Images were acquired of areas of colposcopically normal and abnormal areas of the cervix. Clock positions of the images were noted at the time of imaging. Following surgical excision, the cervical cone specimen was submitted for routine pathology review by a board-certified gynecologic pathologist. Images of stained sections were acquired from regions of tissue imaged with the DSIMe Notwithstanding that any numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. Furthermore, any numerical value noted herein includes a range greater than the specific value noted.

Figure 10:
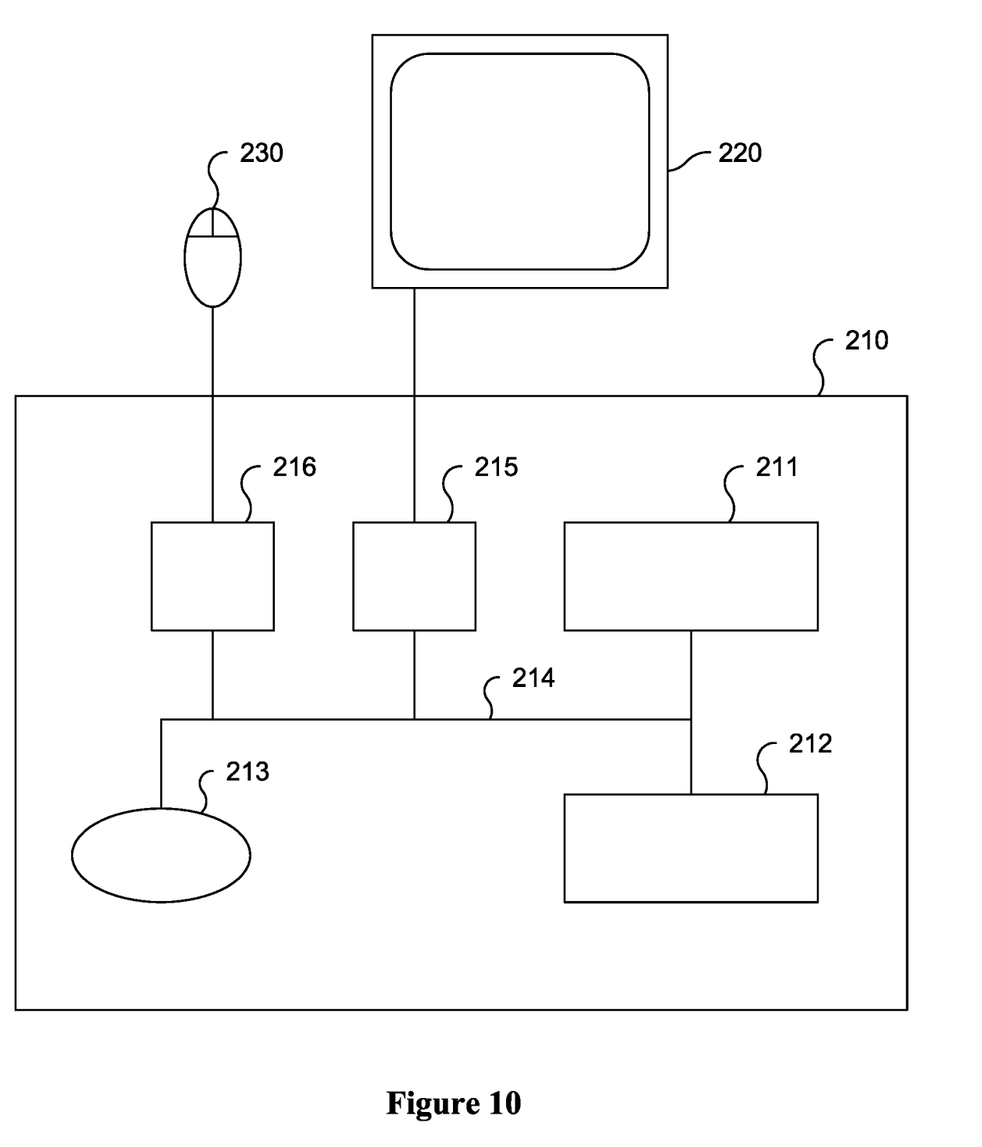
FIG. 10 is a schematic diagram of a computing system of one embodiment of the present disclosure.

One or more of the above-described techniques and/or embodiments can be implemented with or involve software, for example modules executed on or more computing devices 210 (see FIG. 10). Of course, modules described herein illustrate various functionalities and do not limit the structure or functionality of any embodiments. Rather, the functionality of various modules may be divided differently and performed by more or fewer modules according to various design considerations.

Each computing device 210 may include one or more processing devices 211 designed to process instructions, for example computer readable instructions (i.e., code), stored in a non-transient manner on one or more storage devices 213. By processing instructions, the processing device(s) 211 may perform one or more of the steps and/or functions disclosed herein. Each processing device may be real or virtual. In a multi-processing system, multiple processing units may execute computer-executable instructions to increase processing power. The storage device(s) 213 may be any type of non-transitory storage device (e.g., an optical storage device, a magnetic storage device, a solid state storage device, etc. The storage device(s) 213 may be removable or non-removable, and may include magnetic disks, magneto-optical disks, magnetic tapes or cassettes, CD-ROMs, CD-RWs, DVDs, BDs, SSDs, or any other medium which can be used to store information. Alternatively, instructions may be stored in one or more remote storage devices, for example storage devices accessed over a network or the internet.

Each computing device 210 additionally may have memory 212, one or more input controllers 216, one or more output controllers 215, and/or one or more communication connections 240. The memory 212 may be volatile memory (e.g., registers, cache, RAM, etc.), non-volatile memory (e.g., ROM, EEPROM, flash memory, etc.), or some combination thereof. In at least one embodiment, the memory 212 may store software implementing described techniques.

An interconnection mechanism 214, such as a bus, controller or network, may operatively couple components of the computing device 210, including the processor(s) 211, the memory 212, the storage device(s) 213, the input controller(s) 216, the output controller(s) 215, the communication connection(s) 240, and any other devices (e.g., network controllers, sound controllers, etc.). The output controller(s) 215 may be operatively coupled (e.g., via a wired or wireless connection) to one or more output devices 220 (e.g., a monitor, a television, a mobile device screen, a touch-display, a printer, a speaker, etc.) in such a fashion that the output controller(s) 215 can transform the display on the display device 220 (e.g., in response to modules executed). The input controller(s) 216 may be operatively coupled (e.g., via a wired or wireless connection) to an input device 230 (e.g., a mouse, a keyboard, a touch-pad, a scroll-ball, a touch-display, a pen, a game controller, a voice input device, a scanning device, a digital camera, etc.) in such a fashion that input can be received from a user.

The communication connection(s) 240 may enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

FIG. 10 illustrates the computing device 210, the output device 220, and the input device 230 as separate devices for ease of identification only. However, the computing device 210, the display device(s) 220, and/or the input device(s) 230 may be separate devices (e.g., a personal computer connected by wires to a monitor and mouse), may be integrated in a single device (e.g., a mobile device with a touch-display, such as a smartphone or a tablet), or any combination of devices (e.g., a computing device operatively coupled to a touch-screen display device, a plurality of computing devices attached to a single display device and input device, etc.). The computing device 210 may be one or more servers, for example a farm of networked servers, a clustered server environment, or a cloud services running on remote computing devices.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. A high-resolution microendoscope system, comprising:
a fiber optic bundle transmitting light received from a sample,
wherein the light represents a wide-field image of the sample, the wide-field image comprising a sectioned image at a focal depth and a background image at depths different from the focal depth;
a disc receiving the light from the fiber optic bundle, the disc having optical characteristics that cause a transmission of the wide-field image and a reflection of the background image,
wherein the disc comprises a reflective grating,
wherein the light reflected by the reflective grating represents the background image, and
wherein the light passing between the reflective grating represents the wide-field image;
a first camera capturing the wide-field image transmitted through the disc;
a second camera capturing the background image reflected by the disc;
a motor spinning the disc at a speed causing the reflective grating to modulate the light such that the wide-field image and the background image are simultaneously captured by the first and the second cameras, respectively, based on frame rates of the first and second cameras; and
a computer device computing the sectioned image, the computing comprising subtracting the background image from the wide-field image.

2. The high-resolution microendoscope system of claim 1, wherein the fiber optic bundle directly faces the sample without interjacent optical components.

3. The high-resolution microendoscope system of claim 1, further comprising:
a light source; and
a beam splitter disposed between the disc and the first camera to illuminate the sample through the disc with light emitted by the light source.

4. The high-resolution microendoscope system of claim 1, wherein computing the sectioned image further comprises applying a multiplier to one of the background image and the wide-field image to compensate for different optical throughputs to the first camera and the second camera.

5. The high-resolution microendoscope system of claim 1, wherein computing the sectioned image further comprises performing an image stabilization to co-register the wide-field image captured by the first camera and the background image captured by the second camera.

6. The high-resolution microendoscope system of claim 5, wherein the image stabilization is based on a calibration comprising detecting a location of the background image captured by the second camera for different orientations of the disc.

7. A method for high-resolution imaging, the method comprising:
receiving light that represents a wide-field image of a sample, the wide-field image comprising a sectioned image at a focal depth and a background image at depths different from the focal depth;
spinning a disc;
reflecting the background image by a reflective grating of the disc, the disc being exposed to the light;
transmitting the wide-field image through the disc, between the reflective grating;
capturing, by a first camera, the wide-field image transmitted through the disc;
capturing, by a second camera, the background image reflected by the disc,
wherein a speed of the spinning of the disc is selected to modulate the light, by the reflective grating, such that the wide-field image and the background image are simultaneously captured by the first and the second cameras, respectively, based on frame rates of the first and second cameras; and
computing the sectioned image comprising:
subtracting the background image from the wide-field image.

8. The method of claim 7, further comprising:
transmitting the light from the sample by a fiber optic bundle.

9. The method of claim 8,
wherein the fiber optic bundle directly faces the sample without interjacent optical components.

10. The method of claim 7, further comprising:
illuminating the sample through the disc.

11. The method of claim 10,
wherein the illuminating is performed using a light source and via a beam splitter disposed between the disc and the first camera.

12. The method of claim 7,
wherein computing the sectioned image further comprises applying a multiplier to one of the background image and the wide-field image to compensate for different optical throughputs to the first camera and the second camera.

13. The method of claim 7, wherein computing the sectioned image further comprises:
performing an image stabilization to co-register the wide-field image captured by the first camera and the background image captured by the second camera.

14. The method of claim 13,
wherein the image stabilization is based on a calibration comprising detecting a location of the background image captured by the second camera for different orientations of the disc.

15. A high-resolution microendoscope, comprising:
a fiber optic bundle transmitting light received from a sample,
wherein the light represents a wide-field image of the sample, the wide-field image comprising a sectioned image at a focal depth and a background image at depths different from the focal depth;
a disc receiving the light from the fiber optic bundle, the disc having optical characteristics that cause a transmission of the wide-field image and a reflection of the background image,
wherein the disc comprises a reflective grating,
wherein the light reflected by the reflective grating represents the background image, and
wherein the light passing between the reflective grating represents the wide-field image;
a first camera capturing the wide-field image transmitted through the disc;
a second camera capturing the background image reflected by the disc; and
a motor spinning the disc at a speed causing the reflective grating to modulate the light such that the wide-field image and the background image are simultaneously captured by the first and the second cameras, respectively, based on frame rates of the first and second cameras.

16. The high-resolution microendoscope of claim 15, wherein the fiber optic bundle directly faces the sample without interjacent optical components.

17. The high-resolution microendoscope of claim 15, further comprising:
a light source; and
a beam splitter disposed between the disc and the first camera to illuminate the sample through the disc with light emitted by the light source.

18. The high-resolution microendoscope of claim 17, wherein the beam splitter is a dichroic mirror.

19. The high-resolution microendoscope of claim 17, further comprising:
an emission filter disposed between the first camera and the beam splitter.

20. The high-resolution microendoscope of claim 15, further comprising:
an objective lens disposed between the fiber optic bundle and the disc.

* * * * *